(12) United States Patent
Rana et al.

(10) Patent No.: US 11,590,192 B2
(45) Date of Patent: *Feb. 28, 2023

(54) BOTANICAL ANTIOXIDANTS

(71) Applicant: Innophos, LLC, Cranbury, NJ (US)

(72) Inventors: Jatinder Rana, Grand Rapids, MI (US); Kylie Mitchell, Pennington, NJ (US)

(73) Assignee: Innophos, LLC, Cranbury, NJ (US)

( * ) Notice: Subject to any disclaimer, the term of this patent is extended or adjusted under 35 U.S.C. 154(b) by 67 days.

This patent is subject to a terminal disclaimer.

(21) Appl. No.: 17/382,708

(22) Filed: Jul. 22, 2021

(65) Prior Publication Data

US 2021/0346454 A1 Nov. 11, 2021

Related U.S. Application Data

(62) Division of application No. 16/515,091, filed on Jul. 18, 2019, now Pat. No. 11,077,160.

(60) Provisional application No. 62/725,435, filed on Aug. 31, 2018.

(51) Int. Cl.
*A61K 36/77* (2006.01)
*A61P 39/06* (2006.01)
*A61K 31/353* (2006.01)

(52) U.S. Cl.
CPC ............ *A61K 36/77* (2013.01); *A61K 31/353* (2013.01); *A61P 39/06* (2018.01)

(58) Field of Classification Search
None
See application file for complete search history.

(56) References Cited

U.S. PATENT DOCUMENTS 11,297,869 B2 * 4/2022 Rana .................... A61P 3/06
11,311,590 B2 * 4/2022 Rana .................... A61K 36/22

* cited by examiner

*Primary Examiner* — Susan Hoffman
(74) *Attorney, Agent, or Firm* — David LeCroy (57) ABSTRACT

A botanical extract that exhibits antioxidant activity, wherein the botanical extract is at least an extract from the genus *Anacardium*.

5 Claims, 4 Drawing Sheets

Figure 3 (* indicates p<0.05)

Figure 4

BOTANICAL ANTIOXIDANTS

CROSS REFERENCE TO RELATED APPLICATIONS

The present application is a divisional application of U.S. patent application Ser. No. 16/515,091, filed 18 Jul. 2019, now U.S. Pat. No. 11,077,160, which claims the benefit of U.S. Patent Application No. 62/725,435, filed 31 Aug. 2018, the disclosures of which are incorporated herein in their entirety by reference.

BACKGROUND OF THE INVENTION

Field of the Invention

The present invention generally relates to inhibitors of oxidation-induced DNA damage, and more particularly to botanical inhibitors of oxidation-induced DNA damage and the use of such botanical inhibitors as an antioxidant.

Oxygen is a highly reactive atom that is capable of becoming part of potentially damaging molecules called "free radicals". Free radicals, commonly known as reactive oxygen species ('ROS'), contain one or more unpaired electrons in their outermost orbital. Common examples of reactive oxygen species include peroxyl radical (ROO*), superoxide anion ($O_2$*), reactive hydroxyl (OH*), and hydrogen peroxide ($H_2O_2$) radicals. These free radicals are generated spontaneously in living organisms during metabolism. As free radicals are highly unstable, they react with other molecules in their vicinity (e.g., proteins, lipids, or DNA) to attain stability by taking electrons from those molecules, thereby causing damage to the cell and initiating a chain reaction of free-radical generation.

An imbalance between the generation of free radicals and cellular antioxidant can lead to oxidative stress. Oxidative stress occurs when an oxygen molecule splits into single atoms with unpaired electrons, which are called free radicals. Since electrons prefer to be in pairs, these free radicals scavenge the body to seek out other electrons in which to pair with, causing damage to cells, proteins, and DNA in doing so. The term oxidative stress is used to describe the condition of oxidative damage resulting when the critical balance between free radical generation and antioxidant defenses is unfavorable.

Oxidative stress, arising as a result of an imbalance between free radical production and antioxidant defenses, is associated with damage to a wide range of molecular species including lipids, proteins, and nucleic acids. An excess of oxidative stress can lead to the oxidation of lipids and proteins, which is associated with changes in their structure and functions. Short-term oxidative stress may occur in tissues injured by trauma, infection, heat injury, hypertoxia, toxins, and excessive exercise. These injured tissues produce increased radical generating enzymes (e.g., xanthine oxidase, lipogenase, cyclooxygenase) activation of phagocytes, release of free iron, copper ions, or a disruption of the electron transport chains of oxidative phosphorylation, producing excess ROS. Oxidative stress has been implicated in the etiology of several degenerative diseases, such as stroke, Parkinson's disease, Alzheimer's disease, rheumatoid arthritis, diabetes mellitus, peptic ulcer, gene mutations and cancer, heart and blood disorders, and inflammatory diseases. Oxidative stress is now thought to make a significant contribution to all inflammatory diseases (arthritis, vasculitis, glomerulonephritis, lupus erythematous, adult respiratory diseases syndrome), ischemic diseases (heart diseases, stroke, intestinal ischema), hemochromatosis, acquired immunodeficiency syndrome, emphysema, organ transplantation, gastric ulcers, hypertension and preeclampsia, neurological disorder (Alzheimer's disease, Parkinson's disease, muscular dystrophy), alcoholism, smoking-related diseases, and many others.

Antioxidants are capable of stabilizing, or deactivating, free radicals before they attack cells. Application of external source of antioxidants can assist in coping with oxidative stress. These include synthetic antioxidants such as butylated hydroxytoluene and butylated hydroxyanisole; however, these synthetic antioxidants have recently been reported to be dangerous for human health. Thus, the search for effective, nontoxic, natural compounds with antioxidative activity has been intensified in recent years.

Antioxidants are reducing agents, examples of which include nutrient-derived antioxidants such as ascorbic acid (Vitamin C), tocopherols and tocotrienols (Vitamin E), carotenoids, and polyphenols; antioxidant enzymes such as superoxide dismutase, glutathione peroxidase, and glutathione reductase; metal binding proteins such as ferritin, lactoferrin, albumin, and ceruloplasimin; and trace metals (e.g., zinc and molybdenum). These antioxidants can scavenge reactive oxygen species and inhibit the chain reaction by donating an electron to the free radical. The antioxidant defense system, supported by dietary antioxidants, protects the body from free radicals. However, during oxidative stress, antioxidants are insufficient to maintain homeostasis. In such instances, antioxidants can be given as supplements, the consumption of which can significantly reduce the risk for free radical-associated diseases.

Phytomedicine plays an important role in the management of most of these diseases, with plants being a potential source of natural antioxidants. Studies have shown that the consumption of polyphenolic compounds found in tea, fruits, and vegetables is associated with low risk of these diseases. Consequently, there is a growing research interest in plants that contain antioxidants and health-promoting phytoconstituents as potential therapeutic agents. Medicinal plants provide a safe, cost-effective, ecological alternative to chemical antioxidants, which can be toxic on prolonged exposure.

The cashew tree (*Anacardium occidentale* Linn) is originally from the Amazon, and has subsequently been transplanted to India, Eastern Africa, and other countries for cultivation. The tree produces a very peculiar apple or fruit in the form of a swollen peduncle. Externally at the end of this peduncle the cashew nut grows in its own grey colored kidney-shaped hard shell. This shell has a soft leathery outer skin and a thin hard inner skin referred to as the husk or testa, which surrounds the kernel. Between these two skins is a honeycomb structure containing the cashew nut shell liquid. This liquid comprises anacardic acid, cardanol, and cardol, among other ingredients. Anacardic acid is a salicylic acid, while cardanol and cardol are substituted phenols.

The various parts of the fruit have been studied for their uses. In addition to being an edible food, the juice from the cashew apple is used in beverages, while the fruit extract has shown benefit in weight management. Cashew nut shell liquid has been extracted for various industrial and agricultural applications, including friction linings, paints, laminating resins, rubber compounding resins, cashew cements, polyurethane based polymers, surfactants, epoxy resins, foundry chemicals, chemical intermediates, insecticides, and fungicides. Cashew testa has been used in tanning materials.

As part of a healthy lifestyle and a well-balanced, wholesome diet, antioxidant supplementation is recognized as an important means of improving free radical protection. As noted above, there is a need for effective, nontoxic, natural compounds with antioxidant activity. The present invention provides one such solution.

BRIEF SUMMARY OF THE INVENTION

Disclosed herein is a botanical extract comprising catechins, wherein the extract has been standardized to a catechin content of about 15.0 w/w % or greater, based on total weight of the extract, wherein the botanical extract exhibits antioxidant activity, and wherein the botanical extract comprises at least an extract from the genus *Anacardium*. In one aspect, the botanical extract can be obtained from a plant chosen from *Anacardium humile, Anacardium othonianum, Anacardium giganteum, Anacardium nanum, Anacardium negrense* and/or *Anacardium occidentale*. Preferably, the botanical extract is at least from *Anacardium occidentale* L. In one embodiment, the botanical extract is from at least the testa of the fruit of *Anacardium occidentale* L.

In another aspect, the present invention provides a composition containing the botanical extract of the testa of *Anacardium occidentale* L., wherein the botanical extract exhibits anti-oxidant activity. The botanical extract can be present in the composition in an amount of about 4.0 μg/mL or greater. For example, the botanical extract can be present in the composition in an amount of about 4.0 μg/mL to about 2000.0 μg/mL.

In one aspect, the composition containing the botanical extract of the cashew testa inhibits γ-H2AX activity. In one embodiment, the botanical extract is present in the composition in an amount of about 4.0 μg/mL to about 2000.0 μg/mL. Compositions can include, for example, food and/or beverage compositions infused with the extract.

Also provided herein is a dietary supplement having antioxidant properties, wherein the supplement comprises a cashew testa extract in a therapeutically effective amount. For example, the cashew testa extract can be present in the dietary supplement in an amount of about 4.0 μg/mL to about 2000.0 μg/mL.

The present invention further provides a method of inhibiting oxidation-induced DNA damage in a subject by administering a composition comprising the botanical extract of the testa of *Anacardium occidentale* L. at a concentration of about 4.0 μg/mL to about 2000.0 μg/mL.

DETAILED DESCRIPTION OF THE INVENTION

The present invention is based on the surprising discovery that the testa of the cashew (*Anacardium*) is substantially high in certain flavonoids. In particularly, it has been discovered that the extract of cashew testa comprises catechin and epicatechin as major components, as well as procyanidins. Data noted herein demonstrates that cashew testa extract is beneficial in protecting DNA from oxidative stress-induced damage.

For the present application, the term "composition" refers to a product that treats, improves, promotes, increases, manages, controls, maintains, optimizes, modifies, reduces, inhibits, or prevents a particular condition associated with a natural state, biological process or disease or disorder. For example, a composition improves the inhibition of oxidation and/or reduces inflammation, and the like in a subject. The term composition includes, but is not limited to, pharmaceutical (i.e., drug), over-the counter (OTC), cosmetic, food, food ingredient or dietary supplement compositions that include an effective amount of an extract, at least one component thereof, or a mixture thereof. Exemplary compositions include cream, cosmetic lotion, pack or powder, or as an emulsion, lotion, liniment foam, tablets, plasters, granules, or ointment. Compositions can also include beverages, for example, beverages infused with an effective amount of an extract, or a tea satchel containing an effective amount of an extract. Non-limiting examples of food compositions containing an effective amount of an extract include baked goods, protein powders, meat products, dairy products, and confectionary.

As used herein, the term "extract" or "botanical extract" refers to a solid, viscid, or liquid substance or preparation that includes one or more active ingredients of a substance of at least the plant *Anacardium* (e.g., *Anacardium humile, Anacardium othonianum, Anacardium giganteum, Anacardium nanum, Anacardium negrense*, and/or *Anacardium occidentale*), preferably *Anacardium occidentale* L. Preferably, the active ingredient is derived from the extract of the testa of the cashew. The extract can be prepared using a solvent such as water, lower alcohols of 1 to 4 carbon atoms (e.g., methanol, ethanol, butanol, etc.), ethylene, acetone, hexane, ether, chloroform, ethylacetate, butylacetate, dichloromethane, N,N-dimethylformamide (DMF'), dimethylsulfoxide ('DMSO'), 1,3-butylene glycol, propylene glycol, and combinations thereof, but also a fraction of the crude extract in such a solvent. So long as it assures the extraction and preservation of the active ingredient(s), any extraction method may be employed.

As used herein, the term "effective amount" or "therapeutically effective amount" of a pure compound, composition, extract, extract mixture, component of the extract, and/or active agent or ingredient, or a combination thereof refers to an amount effective at dosages and for periods of time sufficient to achieve a desired result. For example, the "effective amount" or "therapeutically effective amount" refers to that amount of a pure compound, composition, extract, botanical extract, extract mixture, botanical extract mixture, component of the extract, and/or active agent or ingredient, or a combination thereof of this invention which, when administered to a subject (e.g., mammal, such as a human), is sufficient to effect treatment, such as improving the inhibition of oxidation and/or reducing inflammation, and the like in a subject. The amount of a composition, extract, botanical extract, extract mixture, botanical extract mixture, component of the extract, and/or active agent or ingredient of this disclosure that constitutes an "effective amount" or "therapeutically effective treatment" will vary depending on the active agent or the compound, the condition being treated and its severity, the manner of administration, the duration of treatment, or the age of the subject to be treated, but can be determined routinely by one of ordinary skill in the art having regard to his own knowledge and to this disclosure.

The term "pharmaceutically acceptable" means those drugs, medicaments, extracts or inert ingredients, which are suitable for use in contact with the tissues of humans and lower animals without undue toxicity, incompatibility, instability, irritation, and the like, commensurate with a reasonable benefit/risk ratio.

The terms "administer", "administered", "administers", and "administering" are defined as providing a composition to a subject via a route known in the art, including but not limited to intravenous, intra-arterial, oral, parenteral, buccal, topical, transdermal, rectal, intramuscular, subcutaneous, intraosseous, transmucosal, or intraperitoneal routes of administration. In preferred embodiments, oral routes of administering a composition are suitable.

As used herein, the term "subject" or "individual" includes mammals to which a composition may be administered. Non-limiting examples of mammals include humans, non-human primates, canines, felines, equines, bovines, rodents (including transgenic and non-transgenic mice) or the like. In some embodiments, the subject is a non-human mammal, and in some embodiments, the subject is human.

As used herein, the term "carrier" refers to a composition that aids in maintaining one or more plant extracts in a soluble and homogeneous state in a form suitable for administration, which is nontoxic and which does not interact with other components in a deleterious manner.

Unless indicated otherwise, all proportions and percentages recited throughout this disclosure are by weight.

The present invention provides a plant-based inhibitor capable of inhibiting DNA damage due to oxidative stress. More particularly, the present invention is directed towards a botanical extract of the cashew testa from the genus *Anacarium*. Such botanical extracts have been found to be capable of inhibiting oxidative stress-induced DNA damage by neutralizing free radicals, thereby terminating the chain reaction created by the free radicals. By terminating the chain reaction, damage due to the free radicals by their reaction with important macromolecules such as DNA, protein, lipids, or the cell membrane is prevented or inhibited.

Useful botanical extracts capable of inhibiting DNA damage due to oxidative stress according to the present invention include botanical extracts from the genus *Anacardium*. More particularly, the plant-based inhibitor is a botanical extract chosen from one or more of the species *Anacardium humile, Anacardium othonianum, Anacardium giganteum, Anacardium nanum, Anacardium negrense*, and/or *Anacardium occidentale*. Preferably, the botanical extract is from the species *Anacardium occidentale*. In one embodiment, the botanical extract is from the testa of the species *Anacardium occidentale*.

Compositions capable of inhibiting DNA damage due to oxidative stress according to the present invention may include one or more compounds that may function as active ingredients. The compound may be a component of the botanical extract. For example, the compound can be a phytochemical present in the plant from which the plant extract is obtained. The compound may be at least partially responsible for inhibiting DNA damage due to oxidative stress. The compound can be any compound capable of inhibiting DNA damage due to oxidative stress. In one embodiment, the compound is chosen from the phytochemicals catechins, epicatechins, and/or procyanidins (e.g., A, B, trimer, tetramer).

Generally, one or more parts of a plant can be used to produce a plant extract including, but not limited to, the root, the stem, the leaf, the flower, the fruit, the seed, and the testa of the seed. In the present invention, at least the testa of the seed is used—alone or with other plant parts—to produce the plant extract. The testa from the *Anacardium* plant can be commercially obtained from various sources. The extract of the cashew testa can be obtained using any suitable extraction technique.

In this regard, one or more parts of the plant, particularly the testa of the plant, can be collected and milled. Thereafter, the milled material can be extracted using a suitable solvent. The solvent can be removed in a concentration step. For example, the extracted material can be screened or filtered to create a supernatant and a cake. The cake can be pressed to remove a substantial portion of the liquid, which can be added to the supernatant. The cake can then be dehydrated and used as a fiber source. The supernatant can be distilled to remove the solvent or a portion thereof, to form a plant extract liquid concentrate. The removed solvent can be recycled. The concentrate can be dried (e.g., by spray drying) to provide a dried plant extract. This dried plant extract can be assayed and/or standardized as described herein. Preferably, the dried plant extract is derived from *Anacardium occidentale*, particularly the testa of the plant *Anacardium occidentale*.

Suitable solvents for the extraction process include water, alcohol, or mixtures thereof. Exemplary alcoholic solvents include, but are not limited to, $C_1$-$C_7$ alcohols (e.g., methanol, ethanol, propanol, isopropanol, and butanol), hydro-alcohols or mixtures of alcohol and water (e.g., hydroethanol), polyhydric alcohols (e.g., propylene glycol and butylene glycol), and fatty alcohols. Any of these alcoholic solvents can be used in the form of a mixture. In one embodiment, the plant extract is extracted using ethanol, water, or a combination thereof (e.g., a mixture of about 70% ethanol and about 30% water). In another embodiment, the plant extract is extracted using only water.

In one embodiment, the plant extract can be obtained using an organic solvent extraction technique. In another embodiment, solvent sequential fractionation can be used to obtain the plant extract. Total hydro-ethanolic extraction techniques can also be used to obtain the plant extract. Generally, this is referred to as a lump-sum extraction.

Total ethanol extraction can also be used. This technique uses ethanol as the solvent. This extraction technique can generate a plant extract having fat soluble and/or lipophilic compounds in addition to water soluble compounds.

Another example of an extraction technique that can be used to obtain the plant extract is supercritical fluid carbon dioxide extraction ('SFE'). In this extraction procedure, the material to be extracted may not be exposed to any organic solvents. Rather, carbon dioxide can be used as the extraction solvent—with or without a modifier—in super-critical conditions (>31.3° C. and >73.8 bar). Those skilled in the art will appreciate that temperature and pressure conditions can be varied to obtain the best yield of extract. This technique can generate an extract of fat soluble and/or lipophilic compounds, similar to a total hexane and ethyl acetate extraction technique.

The plant extract generated in the process can include a broad variety of phytochemicals present in the extracted material. The phytochemicals can be fat soluble or water soluble. Following collection of the extract solution, the solvent can be evaporated, resulting in the extract.

The plant extract can be standardized to a specified amount of a particular compound. For example, the plant extract can be standardized to a specified amount of an active ingredient or phytochemical present in the extract. In one embodiment, the plant extract is standardized to a catechin content of about 15.0 wt % or greater, based on total weight of the extract.

The amount of plant extract present in the oxidative stress-induced DNA damage inhibiting composition can depend upon several factors, including the desired level of oxidative stress-induced DNA damage inhibition, the oxidative stress-induced DNA damage inhibiting level of a particular plant extract or component thereof, and other factors. Preferably, the plant extract is present in an amount of from about 0.005 wt % or greater, for example, from about 0.005 wt % to about 50.00 wt %, based on total weight of the composition.

The oxidative stress-induced DNA damage inhibiting composition can include one or more acceptable carriers. The carrier can aid in enabling incorporation of the plant extract into an oxidative stress-induced DNA damage inhibiting composition having a suitable form for administration to a subject. A wide number of acceptable carriers are known in the art, and the carrier can be any suitable carrier. The carrier is preferable suitable for administration to animals, including humans, and can be able to act as a carrier without substantially affecting the desired activity of the plant extract and/or any active ingredient. The carrier can be chosen based upon the desired administration route and dosage form of the composition.

Suitable dosage forms include liquid and solid forms. In one embodiment, the composition is in the form of a gel, a syrup, a slurry, or a suspension. In another embodiment, the composition is in a liquid dosage form such as a drink shot or a liquid concentrate. In a further embodiment, the composition is present in a solid dosage form, such as a tablet, a pill, a capsule, a dragée, or a powder. When in liquid or solid dosage form, the composition can be in a food delivery form suitable for incorporation into food for delivery. Examples of suitable carriers for use in solid forms (particularly tablet and capsule forms) include, but are not limited to, organic and inorganic inert carrier materials such as gelatin, starch, magnesium stearate, talc, gums, silicon dioxide, stearic acid, cellulose, and the like. The carrier can be substantially inert.

As an example, silicified microcrystalline cellulose can be used as a carrier or binder. Silicified microcrystalline cellulose is a physical mixture of microcrystalline cellulose and colloidal silicon dioxide. One such suitable form of silicified microcrystalline cellulose is ProSolv SMCC® 90, available from Penwest Pharmaceutical Co., Patterson, N.J. Silicon dioxide, in addition to that provided by the silicified microcrystalline cellulose, may be added to the composition as a processing aid. For example, silicon dioxide can be included as a glidant to improve the flow of powder during compression in the manufacturing of solid dosage units, such as tablet.

In another embodiment, the carrier is at least a functional carrier such as buckwheat or spelt. By the addition of functional carriers into the composition, additional benefits may be provided such as lower glycemic index compared to standard carriers such as those mentioned above. Further, functional carriers can be allergan free (e.g., buckwheat), and by adding them into the production process, the botanical extracts of the invention may benefit from the flavonoids of these functional carriers, such as rutin and quercetin. Further, the high fiber content of these functional carriers may also facilitate and regulate intestinal transit. Finally, the added mineral benefit of selenium found in spelt may aid in metabolism.

The oxidative stress-induced DNA damage inhibiting composition can include other inert ingredients, such as lubricants and/or glidants. Lubricants aid in the handling of tablets during manufacturing, such as during ejection from dies. Glidants improve powder flow during tablet compression. Stearic acid is an example of an acceptable lubricant/glidant.

The oxidative stress-induced DNA damage inhibiting composition can be made in solid dosage form, such as tablets and capsules. This form provides a product that can be easily transported by an individual to a place of eating, such as a restaurant, and taken prior to, during, or after consumption of a foodstuff. The composition can be formulated into dosage units containing suitable amounts of the plant extract and/or active ingredient that permit an individual to determine an appropriate number of units to take based upon appropriate parameters, such as body weight, foodstuff size, or carbohydrate (e.g., sugar) content.

In one embodiment, the botanical extract is present in the composition in a therapeutically effective amount, such as an amount of about 4 µg/mL or greater, preferably from about 4.0 µg/mL to about 2000.0 µg/mL, more preferably from about 15.0 µg/mL to about 1000.0 µg/mL, even more preferably from about 30.0 µg/mL to about 500.0 µg/mL. The composition can be administered as a single dose, or in multiple doses. In one example, the compound is administered in up to three doses per day. For example, the compound may be administered prior to a meal, during a meal, or after a meal. In one embodiment, the composition is a dietary supplement having antioxidant properties containing cashew testa extract in a therapeutically effective amount.

The dosage can be chosen to provide a level of inhibitory effect in a single unit that may be effective for some individuals and/or some foodstuffs, while also allowing for relatively simple dosage increases to provide other levels of inhibitory effects that can be effective for other individuals and/or other foodstuffs.

The inhibiting composition can be in a form adapted for oral ingestion. This form can be configured as a single dosage form intended to provide a specified dose of the plant extract. For example, the single dosage form can be a powder, a pill, a tablet, a capsule, or a drink shot. The single dosage form can include, for example, from about 4.0 µg/mL to about 2000.0 µg/mL of the plant extract.

EXAMPLES

Examples—Materials and Chemical Profiling

Example 1—Preparation of Cashew Testa Extract Using 70% Ethanol Solvent

Dried cashew testa powder (*Anacardium occidentale*) (60 g) was loaded into three 100 ml stainless steel tubes and extracted twice using a solvent of 70% ethanol in DI water with a Thermo Scientific™ Dionex™ ASE 350 Accelerated Solvent Extractor at a temperature of 80° C. and pressure of 1500 psi. The extract solution was filtered and collected. The combined ethanol extract solution was evaporated with a rotary evaporator under vacuum to give a crude cashew testa extract.

The extraction results are provided in the following Table 1—

TABLE 1

Extraction of cashew testa

| Plant Part | Plant Powder (g) | Extract Weight (g) | Extraction Yield (wt %) |
|---|---|---|---|
| Testa | 60 | 23.78 | 39.63% |

Example 2—Catechin Quantification of Cashew Testa Extract

Free catechins present in the cashew testa extract were determined using a C18 reversed-phase column (Luna® 5 µm C18(2) 100 Å LC Column 250×4.6 mm, available from Phenomenex®, Torrance, Calif., US) together with an Hitachi high performance liquid chromatograph with photodiode array detector ('HPLC/PDA'). For mobile phase A, the solvent was 0.10% phosphoric acid ('$H_3PO_4$') in water, and for mobile phase B, the solvent B was acetonitrile ('ACN'), which was used for elution at a flow rated of 1.0 ml/min with UV absorbance at 275 nm and a column temperature of 35° C. Catechin reference standards used were from Sigma-Aldrich Co. The reference standards were dissolved in methanol ('MeOH'): 0.1% $H_3PO_4$ (1:1 ratio) with catechin (C1251) at a concentration of 0.5 mg/ml and epicatechin (E1753) at 0.1 mg/ml. Testing samples were prepared at 2 mg/ml in 50% MeOH in 0.1% $H_3PO_4$ in a volumetric flask and sonicated until dissolved (approximately 10 minutes), and then cooled to room temperature, mixed well, and filtered through a 0.45 µm nylon syringe filter. HPLC analysis was performed by injecting a 20 µl sample into the HPLC. Table 2 below provides the gradient table of HPLC analytical method—

TABLE 2

Gradient Table of HPLC Analytical Method

| Time (min) | Mobile Phase A | Mobile Phase B |
|---|---|---|
| 0.0 | 85.0 | 15.0 |
| 7.0 | 85.0 | 15.0 |
| 12.0 | 10.0 | 90.0 |
| 16.5 | 10.0 | 90.0 |
| 16.6 | 85.0 | 15.0 |
| 24.0 | 85.0 | 15.0 |

Figure 1:
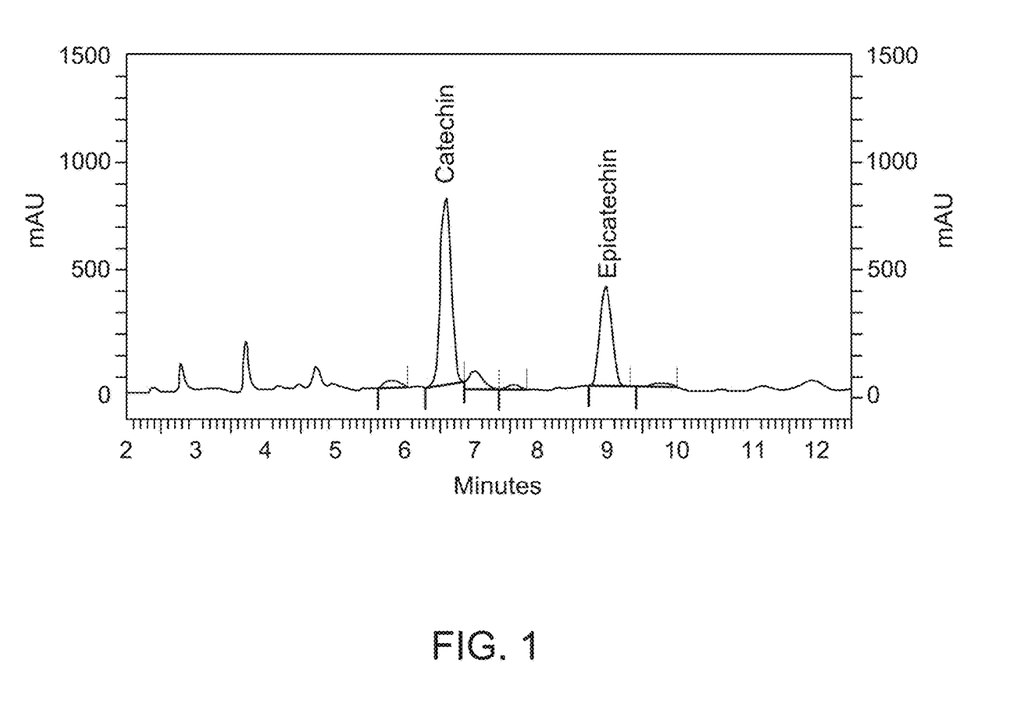
FIG. 1 is an HPLC chromatogram of cashew testa extract at 275 nm over a retention time of from 0 minutes (start) to 20 minutes.

HPLC Catechin quantification results in cashew testa extract provided a catechin content of 9.40% and an epicatechin content of 6.12%, for a total catechin content of 15.52% by weight, based on total weight of the extract. Accordingly, the cashew testa extract can be standardized to a total catechin content of about 15.00% or greater by weight, based on total weight of the extract. The HPLC chromatogram for cashew testa extract at 275 nm wavelength is provided in FIG. 1.

Example 3—Chemistry Profiling of Cashew Testa Extract

Flavonoid compounds present in the cashew testa extract were determined using ultra high pressure liquid chromatography ('HPLC') and mass spectrometry (ACQUITY® UPLC I-Class and XEVO® GS-XT-QTof system, both available from Water Corporation, Milford, Mass. USA). The column used was an ACQUITY® UPLC HSS T3 2.1×100 mm, 1.8 µm, with a column temperature of 40° C. and a sample temperature of 15° C. For the mobile phase, Solvent A was 10% acetonitrile ('ACN') in water (0.1% Formic Acid), and Solvent B was ACN. The acquisition range was 100-1500 Daltons ('Da'), and the acquisition mode was electrospray ionization ('ESI') (−). Table 3 below provides the HPLC conditions—

TABLE 3

HPLC conditions for analyzing cashew testa extract

| Run Time (min) | Injection Volume (µL) | Concentration |
|---|---|---|
| 20.00 | 2.00 | 1 mg/mL |

Figure 2:
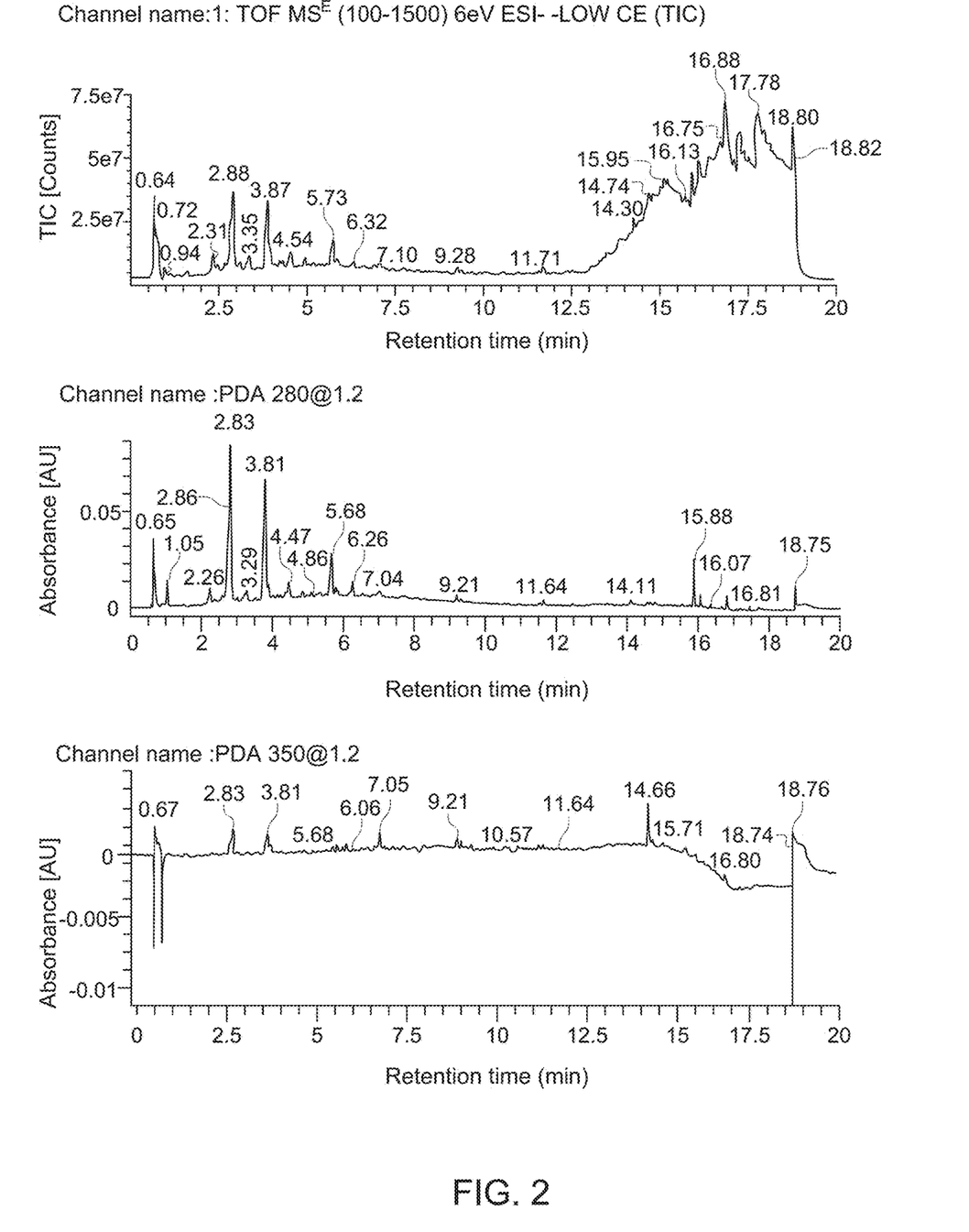
FIG. 2 is LC/MS and LC/PDA (wavelengths of 280 and 350 nm) chromatograms of cashew testa extract.

Peak identification was based on accurate mass only. Digalloyl catechin, catechin and epicatechin were identified as the major components for cashew testa extract. Procyanidins were detected in the extract as well, including A- and B-type procyanidins, procyanidin tetramer, and procyanidim trimer, with B-type procyanidins being the major component of the procyanidins. Compounds identified, in addition to those just mentioned, included digalloyl catechin, vacciheim A, 6"-p-coumaroylprunin, and dunalianoside B, among others. LC/MS and LC/PDA chromatograms of cashew testa extract obtained from the analysis are illustrated in FIG. 2.

Examples—Bioassay

Extracts of cashew testa were prepared with food-grade ethanol, and then filtered and dried as described above. Research grade reagents were used for the rest of the assay preparations. Extracts were dissolved in dimethyl sulfoxide ('DMSO') to a final concentration of 50 mg/mL, and then diluted in appropriate buffer for each bioassay to working concentrations.

Example 4—DNA Damage Assay

When DNA damage—whether endogenous or exogenous—forms double stranded breaks ('DSBs'), it is always followed by phosphorylation of the histone H2AX. H2AX is a variant of the H2A protein family, which is a component of the histone octomer in nucleosomes. It is phosphorylated by kinases such as ataxia telangiectasia mutated ('ATM') and ATM-Rad3-related ('ATR') in the PI3K pathway. The protein γ-H2AX is the first step in recruiting and localizing DNA repair proteins. DSBs can be induced by mechanisms such as ionizing radiation or cytotoxic agents and subsequently, γ-H2AX foci quickly form. These foci represent the DSBs in a 1:1 manner and can be used as a biomarker for damage. An antibody can be raised against γ-H2AX, which can therefore be visualized by immunofluorescence through secondary antibodies The detection and visualization of γ-H2AX by flow cytometry allow the assessment of DNA damage, related DNA damage proteins, and DNA repair.

Human skin fibroblasts were seeded at a density of 8000 cells/well in 96-well tissue culture plates. After 24 hours, cells were treated with test compounds for 48 hours, after which the cells were treated with 1 mM hydrogen peroxide for 4 hours to induce DNA damage. Hydrogen peroxide induces DNA damage by creating breaks in the DNA. Cells were then fixed and stained with an antibody to the biomarker γ-H2AX, which is a phosphorylated histone variant that is found at double-strand breaks. At sites of double-strand breaks, the histones are phosphorylated, indicating that the DNA is damaged and requires repair. An antibody for γ-H2AX—the phosphorylated histone variant—is useful in identifying sites of DNA damage. Nuclei were stained with 4',6-diamidino-2-phenylindole ('DAPI'), which is a fluorescent stain that binds to DNA. Pictures were taken with Image Xpress and analyzed with Meta Xpress to measure fluorescence intensity in each condition divided by the total number of cells.

Figure 3:
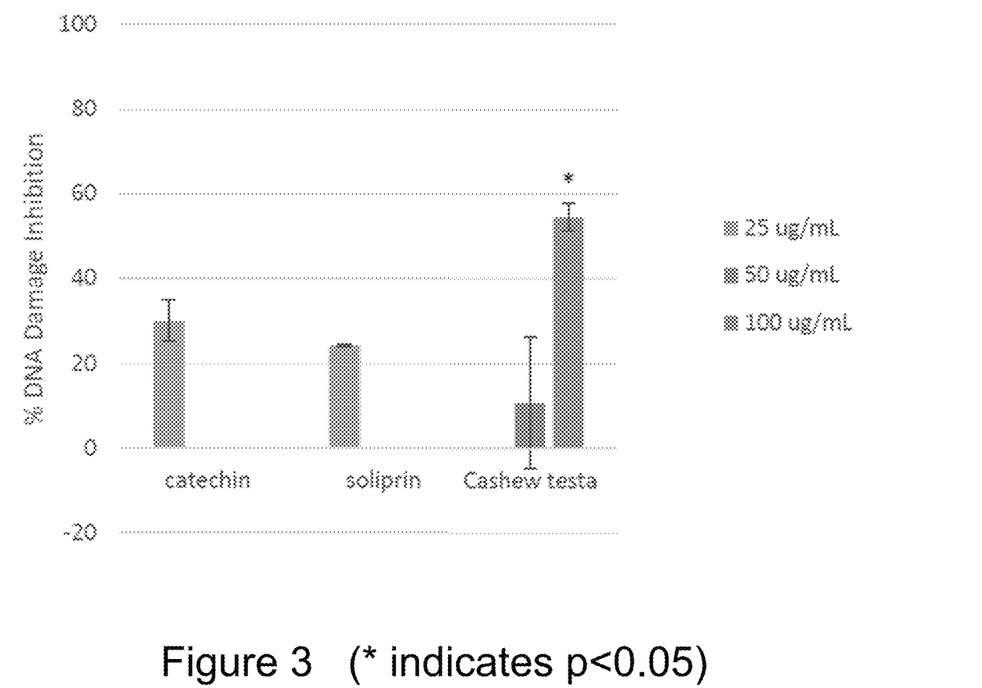
FIG. 3 is a graph illustrating the efficacy of cashew testa extract in inhibiting DNA damage compared to catechin and soliprin standards.

DNA damage in response to hydrogen peroxide treatment was measured by the amount of γ-H2AX present in cells. Cashew testa extract was tested for DNA damage inhibition at 50 and 100 µg/mL based on the amount of γ-H2AX detected after treatment with hydrogen peroxide to induce DNA damage. Catechin and soliprin at 25 µg/mL were used as positive controls. As shown in FIG. 3, cashew testa extract at 100 µg/mL exhibited significant protection of DNA from damage in response to hydrogen peroxide treatment. Percent inhibition was calculated relative to wells that were not treated with extracts but were exposed to hydrogen peroxide. From this Example, it is seen that pre-treating fibroblasts with cashew testa extract at 100 µg/mL significantly reduced the amount of γ-H2AX detected, showing the ability of cashew testa extract to protect DNA from oxidative stress-induced damage.

Figure 4:
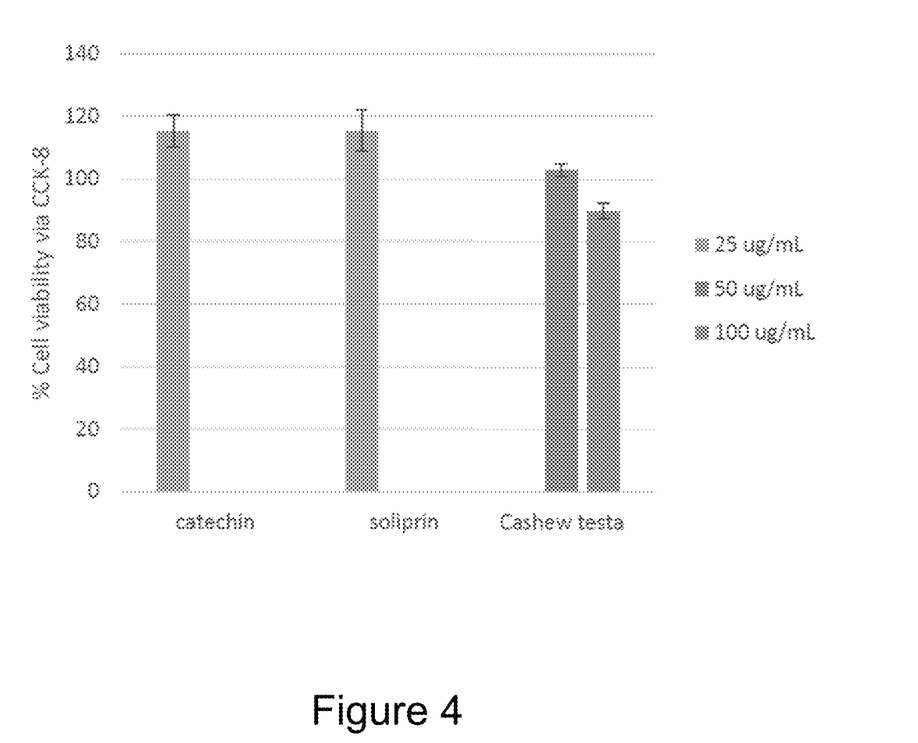
FIG. 4 is a graph illustrating cell viability of a cell culture when dosed with various doses of cashew testa extract versus catechin and soliprin standards.

Cell Counting Kit-8 ('CCK-8') was used to determine the percentage of viable cells in each treatment relative to an untreated control. CCK-8 reagent was added to the media (final concentration 10% total volume) and incubated for one (1) hour at 37° C. and 5% CO2 before absorbance was read on a Multimode Reader at 460 nm to determine the number of viable cells relative to untreated control wells. The cashew testa extract treatment was not statistically significantly different from the untreated controls (FIG. 4) and therefore not toxic to human skin fibroblasts.

The above data illustrates that the botanical extract of the testa of *Anacardium occidentale* L. has one or more compounds that exhibit anti-oxidant activity. More particularly, the cashew testa extract may have reasonable activities in ameliorating γ-H2AX activity.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Further, unless defined otherwise, all technical and scientific terms used herein have the same meaning as commonly understood to one of ordinary skill in the art to which this invention belongs. Consequently, it is not intended that this invention be limited to the specific embodiments disclosed herein, but that it cover all modifications and alternatives coming within the true scope and spirit of the invention as embodied in the attached claims.

We claim:

1. A method of inhibiting oxidation-induced DNA damage in a subject comprising:
    administering a composition comprising a botanical extract of the testa of the seed of *Anacardium occidentale* L.,
    wherein the botanical extract is present in the composition in a therapeutically effective amount of about 30.0 µg/mL to about 500.0 µg/mL,
    wherein the botanical extract has been standardized to a catechin content of about 15.0 w/w % or greater, based on total weight of the extract, and
    wherein the composition inhibits oxidation-induced DNA damage.

2. The method according to claim 1 wherein the composition is a dietary supplement.

3. The method according to claim 1 wherein the composition is a beverage.

4. The method according to claim 1 wherein the composition is a food composition.

5. The method according to claim 1, wherein the composition is a dietary supplement.

* * * * *